US00PP31470P2

(12) United States Plant Patent
Stoppel

(10) Patent No.: US PP31,470 P2
(45) Date of Patent: Feb. 25, 2020

(54) ***PRUNUS* TREE NAMED 'FINAL 131'**

(50) Latin Name: ***Prunus avium* L.**
Varietal Denomination: Final 131

(71) Applicant: Peter Stoppel, Kressbronn (DE)

(72) Inventor: Peter Stoppel, Kressbronn (DE)

(73) Assignee: Peter Stoppel, Kressbronn (DE)

( * ) Notice: Subject to any disclaimer, the term of this patent is extended or adjusted under 35 U.S.C. 154(b) by 0 days.

(21) Appl. No.: 16/501,384

(22) Filed: Apr. 4, 2019

(51) Int. Cl.
*A01H 5/08* (2018.01)
*A01H 6/74* (2018.01)

(52) U.S. Cl.
USPC ..... Plt./181

(58) Field of Classification Search
USPC ..... Plt./181
CPC ..... A01H 5/08; A01H 6/74
See application file for complete search history.

*Primary Examiner* — Annette H Para
(74) *Attorney, Agent, or Firm* — Myers Bigel, P.A.

(57) ABSTRACT

'Final 131' is a new cultivar of *Prunus avium* having a medium-strong tree habit, self-fertile flowers, S-alleles S3S4, heart-shaped fruit with a black-red color, a fruit ripening time that is later its male parent 'Sweetheart', and fruit that is bigger in size than 'Sweetheart'.

2 Drawing Sheets

Latin name of the genus and species: The Latin name of the novel plant variety disclosed herein is *Prunus avium* L.

Variety denomination: The inventive *Prunus avium* tree disclosed herein has been given the varietal denomination 'Final 131'.

BACKGROUND OF THE INVENTION

The present invention comprises a new and distinct *Prunus avium* cultivar hereinafter referred to by the cultivar name 'Final 131'. This new *Prunus* cultivar was developed through a breeding program in Baden Wuerttemberg, Germany with the goal of producing good quality fruit with a late ripening time. 'Final 131' was selected from a population of seedlings grown from a controlled cross of *Prunus avium* 'Spate von Wedler' (unpatented, female parent) x *Prunus avium* 'Sweetheart' (unpatented, male parent). The first asexual propagation of 'Final 131' was carried out in 2006 by hardwood cuttings in Germany and has been asexually reproduced repeatedly by hardwood cuttings since then. 'Final 131' has been found to retain its distinctive characteristics through successive asexual propagations.

SUMMARY OF THE INVENTION

The following are the unique combination of characteristics of this new cultivar when grown under standard horticultural practices in Germany.

- 'Final 131' has less cracking of the fruit than 'Sweetheart'.
- 'Final 131' has a later fruit ripening time than 'Sweetheart'.
- 'Final 131' has S-alleles S3S4 and self-fertile flowers.
- 'Final 131' has fruit which are black-red in color and bigger in size than 'Sweetheart'.
- 'Final 131' has a medium strong tree habit.

BRIEF DESCRIPTION OF THE DRAWINGS

This new *Prunus* cultivar is illustrated by the accompanying photographs which show the plant's fruit and foliage.

The colors shown are as true as can be reasonably obtained by conventional photographic procedures. Colors in the photographs may differ slightly from the color values cited in the detailed botanical description, which accurately describe the colors of the new *Prunus* cultivar.

DETAILED BOTANICAL DESCRIPTION

Figure 1:
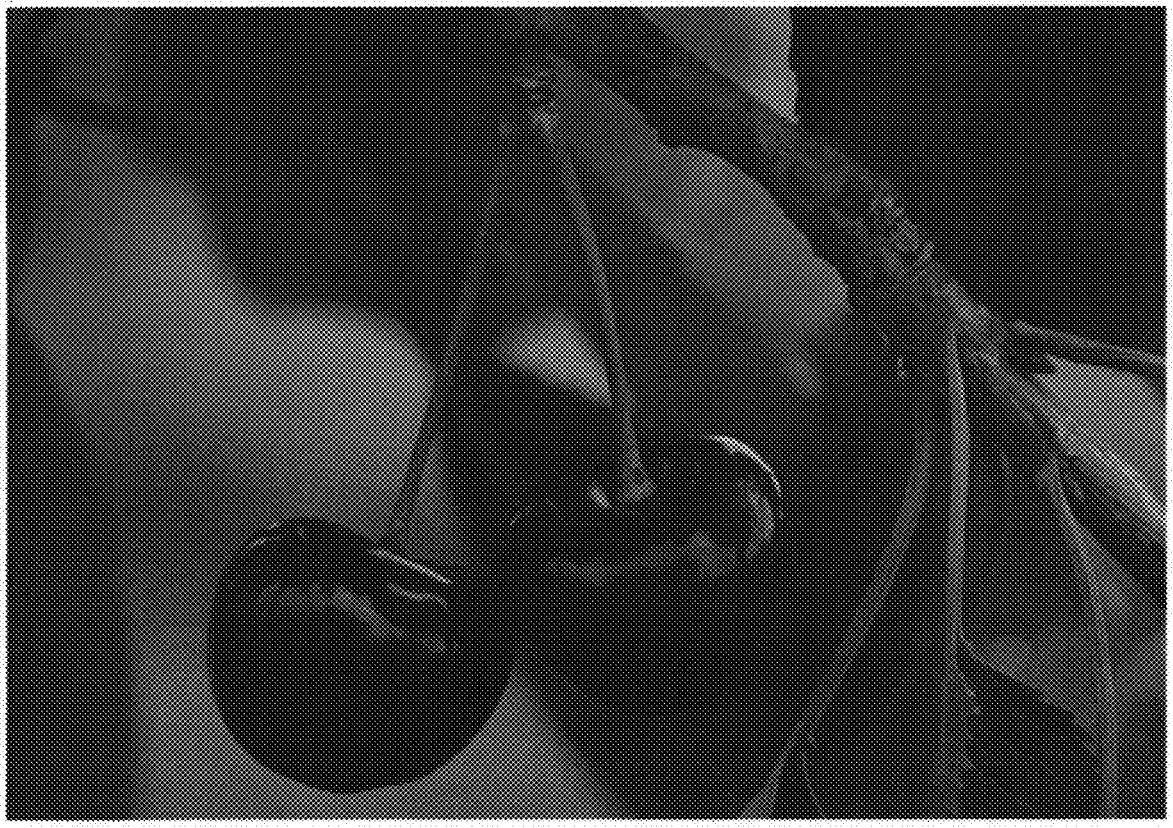
FIG. 1 is a color photograph showing the fruit on a seven-year-old tree of 'Final 131'.
Figure 2:
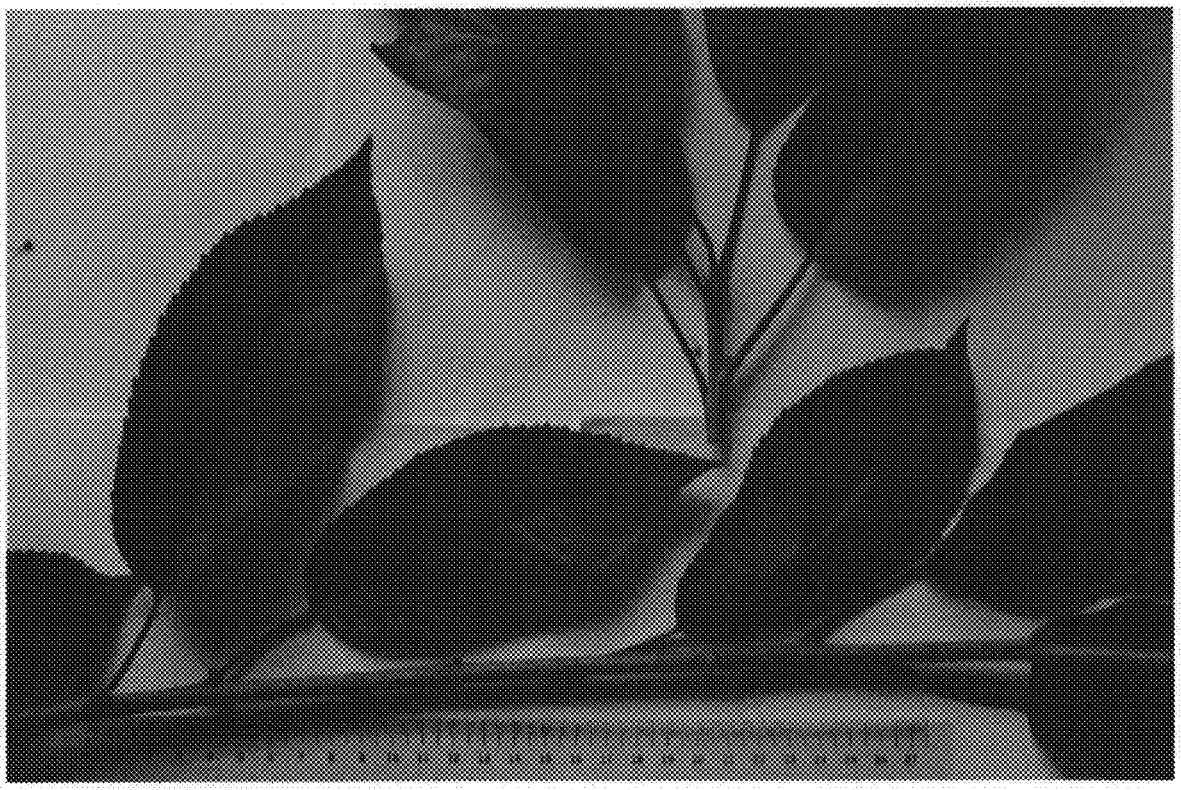
FIG. 2 is a color photograph showing the foliage (upper surface) from a seven-year-old tree of 'Final 131'.

The following is a detailed description of the botanical characteristics of the new and distinct *Prunus* cultivar known by the denomination 'Final 131'. The detailed description was taken on a seven-year-old tree in Germany. All colors cited herein refer to The Royal Horticultural Society Colour Chart (The Royal Horticultural Society (R.H.S.), London, 2005 Edition). Where specific dimensions, sizes, colors, and other characteristics are given, it is to be understood that such characteristics are approximations or averages set forth as accurately as practicable.

TECHNICAL DESCRIPTION OF THE VARIETY

Classification:

*Botanical name.*—*Prunus avium* 'Final 131'.

Parentage: Seedling grown from a controlled cross of *Prunus avium* 'Spate von Wedler' (unpatented, female parent) x *Prunus avium* 'Sweetheart' (unpatented, male parent).

Plant description:

*Size.*—Height about 3 m, width about 2 m (10 cm above ground).

*Vigor.*—Medium.

*Density.*—Medium.

*Form.*—Upright spread with medium level of lateral branching.

*Growth type.*—Spreading.

*Bearing.*—Annual on spurs and 3 and 4 bud positions located at the base of one year old shoots.

Trunk:

*Size*.—Medium.

*Surface texture*.—Smooth with prominent lenticels.

*Bark color*.—Moderate olive brown 199A.

*Lenticels*.—Length: 1-2 cm. Width: 0.5 cm. Color: grayed orange 167A. Density: medium.

Branches:

*Diameter*.—0.5-1.5 cm.

*Surface texture*.—Average, typical for Sweet Cherry.

*Color*.—Brownish orange 164A.

*Form*.—Typical for Sweet Cherry.

*Average angle*.—60-75 degree.

*Bud arrangement*.—Typical for Sweet Cherry.

*Lenticels*.—Length: about 1 mm. Width: about 1 mm. Shape: roundish. Density: few, scattered. Color: grayed yellow 161B.

Leaves:

*Length*.—15-18 cm.

*Width*.—7-8 cm.

*Form*.—Narrow, pointed.

*Texture*.—Leathery, crisp feeling.

*Thickness*.—Medium.

*Base*.—Pointed.

*Apex*.—Pointed.

*Margin*.—Serrations irregular.

*Color*.—Mature leaves: Upper surface: vivid yellowish green 134A. Lower surface: very pale green 130D.

*Petiole*.—Shape: narrow. Length: 4-5 cm. Diameter: about 2 mm. Color: brilliant yellowish green 149C.

*Veins*.—Venation type: pinnate. Color: Upper surface: light yellowish green 154D.

Flower buds:

*Pedicel*.—Length: 20 mm. Diameter: 0.4 mm. Color: reddish.

*Bud*.—Length: about 1 cm. Width: under 1 cm. Color: reddish.

Flowers:

*Bloom timing*.—22.04. Kressbronn, Germany.

*Blooming period*.—Medium-early season, with Burlat.

*Pollination requirements*.—Self-fertile.

*Number of flowers per raceme*.—3 to 7.

*Petals*.—Number: 5. Length: 13-17 mm. Width: 11-15 mm. Shape: apex rounded, round shape, shell like. Apex: slightly obcordate. Margin: entire. Texture and appearance: smooth texture.

*Color*.—Fully opened: Upper surface: White 155D. Lower surface: White 155D.

*Sepals*.—Shape: elongated. Margin: entire. Texture: smooth. Length: 6 mm. Width: 2-4 mm. Color: Upper surface: Green 146C. Lower surface: Green 146C.

*Stamens*.—Number (per flower): 4-5. Filament length: 0.8 mm.

*Anthers*.—Shape: kidney. Length: 0.6 mm. Color: 167A.

*Pollen*.—Color: yellow 13B. Amount (generally): plentiful.

*Pistils*.—Length: 9 mm.

*Style*.—Length: 8 mm. Color: green 144A.

*Stigma*.—Shape: round. Color: green 144A.

Fruit:

*Maturity when described*.—10.08.16 (23 days after Regina in south Germany).

*Size*.—Diameter: 3 cm. Length: 3.1 cm.

*Skin*.—Thickness: medium. Texture: slightly orange skin. Tendency to crack: not prone to cracking from rain. Color: dark red 53A.

*Flesh*.—Aroma: pleasant. Color: strong reddish orange 40C. Texture: very firm. Eating quality: good.

*Seeds*.—Number per fruit: 1. Length: 1.3 cm. Breadth: 0.7-0.9 cm. Form: round. Color: light brown 160B.

*Stem*.—Length: 4.5 cm. Width: 0.1 cm. Color: light green 145A.

COMPARISON OF 'FINAL 131' WITH COMMERCIAL CULTIVARS AND PARENTAL PLANTS

'Final 131' is similar to its male parent, 'Sweetheart', in that both have S-alleles S3S4, are self-fertile and have a medium strong tree habit. 'Final 131' is distinct from 'Sweetheart' by its longer stem length, larger fruit size, and a fruit ripening time that is ten days later. In addition, the fruit color of 'Final 131' is black-red compared to the more brown black color of the fruit of 'Sweetheart'.

'Final 131' is distinct from the *Prunus* cultivar 'Tieton' (U.S. Pat. No. 11,385), by its S-alleles, which are S3S9 compared to S-alleles S3S4 in 'Final 131'. 'Final 131' is 20 days later in fruit ripening than 'Regina' (not patented). The fruit shape of 'Final 131' is heart-shaped compared to 'Regina', which has a more round-shaped fruit. 'Final 131' has firmer fruits than 'Regina'. Flowering in 'Final 131' is medium-early in flowering compared to 'Regina', which is very late.

What is claimed is:

1. A new and distinct *Prunus* tree named 'Final 131' substantially as illustrated and described herein.

* * * * *